(12) United States Patent
Amos, Jr. et al.

(10) Patent No.: US 6,231,542 B1
(45) Date of Patent: *May 15, 2001

(54) SUTURE RETENTION DEVICE

(75) Inventors: Raymond George Amos, Jr., Spencer; Srinivas Nishtala, Bloomington; Jeffrey Carl Smith, Poland, all of IN (US); John Edward Crowley, Southborough, MA (US)

(73) Assignee: Boston Scientific Corporation, Natick, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/299,407

(22) Filed: Apr. 26, 1999

Related U.S. Application Data

(63) Continuation of application No. 08/921,439, filed on Aug. 29, 1997, now Pat. No. 5,941,849.

(51) Int. Cl.[7] .................................................. A61M 37/00
(52) U.S. Cl. ............................................................ 604/95.01
(58) Field of Search ............................. 604/95, 174, 178, 604/280, 27, 51, 93, 264, 34, 242, 249, 281

(56) References Cited

U.S. PATENT DOCUMENTS

| | | | |
|---|---|---|---|
| 5,928,208 | * | 7/1999 | Chu et al. .............................. 604/280 |
| 5,941,849 | * | 8/1999 | Amos, Jr. et al. ...................... 604/95 |

* cited by examiner

Primary Examiner—Sharon Kennedy
Assistant Examiner—Ann Y. Lam
(74) Attorney, Agent, or Firm—George A. Herbster; Pearson & Pearson

(57) ABSTRACT

A control mechanism for a catheter with a distal anchor. Suture threads extend from the anchor to the control mechanism. A first body contains a reel with a radial port through which the suture threads extend to be received in a termination structure on a second, partially concentric and axially coextensive body of the control mechanism. Rotation of the second body wraps and unwraps the sutures about the reel thereby to remove or introduce slack into the suture threads after the anchor device forms. Removing slack in the suture threads prevents complete straightening of the anchor device and therefore inadvertent removal of the catheter from the patient.

5 Claims, 7 Drawing Sheets

SUTURE RETENTION DEVICE

This application is a continuation, of application Ser. No. 08/921,439, filed Aug. 29, 1997, now U.S. Pat. No. 5,941,849, issued Aug. 24, 1999.

BACKGROUND OF THE INVENTION

1. Field of the Invention

This invention generally relates to the field of catheters and more particularly to a catheter having a mechanism for retaining a distal end of the catheter in a predetermined configuration.

2. Description of Related Art

There are a variety of therapies or treatment modalities that require a catheter with a distal anchor or the like to retain the catheter in position. One particular application involves catheters used for drainage purposes. For example, procedures for the suprapubic catheterization of the bladder drain the bladder after surgery or when the genitourinary system is plugged by an obstruction. Procedures using other percutaneously inserted catheters are also used to drain the kidney or biliary system as well as to drain abscesses, other sites of fluid collection and other viscera. Still other procedures use percutaneously inserted catheters as gastrostomy feeding tubes.

Generally these catheters are introduced into a patient through a large hypodermic needle or trocar. A guidewire is inserted through the needle or trocar which is then removed. The catheter tube, with a stiffening cannula, passes over the guidewire into the cavity. The cannula and guidewire can then be withdrawn leaving a portion of the catheter at its distal end in the desired cavity.

It is very easy to withdraw one of these catheters by movement of the body or under other conditions. Also these catheters generally have side ports at the distal end that can be inadvertently drawn into the abdominal cavity creating potential for severe infections when the catheter is inserted for bladder treatment.

Various catheters have been developed with diverse anchor structures to prevent inadvertent removal of the catheter from a patient. One such anchor is a "pigtail loop" formed by a flexible tube portion at the distal end of the catheter. The loops have a number of ports to ensure drainage. Generally the pigtail loop is preformed in the catheter because the flexible tube of the catheter is formed of a memory material. For introduction into a patient, a stiff cannula or similar implement is inserted through the catheter lumen to straighten the pigtail loop. The distal end of the flexible tube returns to the pigtail loop configuration after the cannula is removed.

Typically a suture thread extends through draw ports at two spaced positions along the distal portion of the flexible tube. These portions come into juxtaposition when the pigtail loop forms after the surgeon removes the cannula. Then the surgeon will take up any slack in the one or more suture threads that lead distally from the pigtail loop. When a suture thread is taut, it prevents the pigtail loop from straightening by holding the juxtaposed portions of the catheter together. Even taking up a portion of the slack can prevent complete straightening of the pigtail loop or other anchor.

When it is appropriate to remove the catheter, a cannula is inserted through the catheter from the proximal end until it encounters the pigtail loop. Then the suture threads are released and the stiff cannula can then be advanced to straighten the pigtail loop and facilitate the removal of the catheter from the patient.

With some catheters the proximal end of the suture thread is locked or retained in place by placing a hollow cap onto or over the proximal end of the catheter tube after the suture thread has been drawn into a taut condition. This structure traps the proximal end of the suture thread. Any protruding portion of the suture thread can then be cut if desired. Trapping or locking the suture thread prevents the pigtail loop from straightening.

With other catheters the suture thread is trapped between two or more hollow tubes one of which is slidably inserted axially into the other. A short length of suture thread generally is left hanging from the catheter so that if it becomes loose, it may be retightened. For example, U.S. Pat. No. 5,041,085 to Osborne et al. discloses a lockable sleeve drainage catheter with a flexible distal end that can form a pigtail loop. A locking sleeve positioned at the proximal end of the catheter draws the suture thread through a passageway to retain the distal end in the pigtail configuration. A locking collar at the proximal end of the elongated member tube has an annular recess formed therein. An annular step at the distal end of the lockable sleeve engages the recess to lock the sleeve in a fixed position. When fully extended and locked, the sleeve and elongated member form a fluid tight connection to prevent any leakage of fluids being drained.

U.S. Pat. Nos. 4,643,720 and 4,740,195 to Lanciano disclose alternative embodiments of a mechanism specifically designed for retaining the distal end of a catheter in a pigtail loop. As particularly shown in the later patent, a suture thread, as a flexible link, extends through a member that, when rotated, wraps the suture thread about the circumference thereof. Consequently after the distal end of the catheter forms the pigtail loop, rotating the member tensions the suture thread to prevent the pigtail loop from straightening.

U.S. Pat. No. 5,419,764 to Roll discloses still another structure that incorporates a twisting suture thread lock. The twisting lock is positioned at the proximal end of the catheter to draw the suture thread or flexible link through the passageway of the catheter after the distal end of the flexible tube forms the pigtail loop. Twisting the proximal member relative to the distal member of the twisting locking device causes the suture to wrap around a reel within the device. Once the locking mechanism tightens the suture thread and reaches its locked position, a rubber O-ring is compressed resulting in a fluid tight connection. The friction exerted between the O-ring and the adjacent members prevents unlocking of the system and unwinding of the suture thread.

Controlling steerable catheters constitute another class of catheters with deflectable tips that use suture threads as flexible links, but for steering purposes. For example, U.S. Pat. No. 5,030,204 to Badger et al. discloses an axially displaceable manipulator that displaces a control line to deflect a distal tip and decrease the included angle between the distal portion and main portion of a shaft. Thus adjusting the control line position enables the catheter to steer the catheter by deflecting the catheter tip.

U.S. Pat. No. 5,185,004 to Lashinski discloses another mechanism including a translational nut mechanism for limiting the number of turns that can be applied to a steerable guidewire. Stops to proximal and distal motion of the nut provide the limit.

Each of the foregoing Lanciano, Osborne et al. and Roll references discloses a locking or retention mechanism for maintaining the pigtail of a drainage catheter in a locked or retention position. However, each has certain disadvantages. For example, each of the retention mechanisms is formed as a housing with internally moving parts. The assembly of such mechanisms, particularly when it is desired to maintain a sealed environment, introduces complicated process or manufacturing steps that can increase the overall expense of the final catheter to prohibitive levels. Moreover, each involves locating a somewhat enlarged structure at the proximal end of the catheter that can be cumbersome to use and increase patient discomfort. Certain of these mechanisms are also subject to patient manipulation.

SUMMARY

Therefore it is an object of this invention to provide a locking mechanism for the tension member in a drainage catheter or the like that has a low profile, is compact and easy to use.

Another object of this invention is to provide a locking mechanism for a flexible tension member in a drainage catheter that includes a minimum number of components, particularly internal components.

Still another object of this invention is to provide a locking mechanism for the flexible tension member of a drainage catheter that minimizes the potential for the undesirable leakage of the drainage fluid therefrom.

Still another object of this invention is to provide a locking mechanism for a drainage catheter tensioning member that is easy to manufacture.

In accordance with this invention a catheter assembly comprises a flexible tube having a lumen therethrough extending between distal and proximal ends and forming into a pigtail loop at the distal end when unrestrained. The distal end has at least two spaced ports for enabling the retention of said pigtail loop. This catheter assembly includes a first body affixed to the proximal end of the flexible tube. The first body has an axial passage as an extension of the lumen and a reel disposed at the proximal end with a radial aperture therethrough. A suture extends through the two spaced ports, the lumen and the radial aperture. A second body, that is concentric with a portion of said first body, includes an axial passage as an extension of the axial passage through the first body and a termination for receiving the ends of the suture threads extending from the radial aperture. A structure intermediate the first and second bodies enables the rotation of the second body without axial displacement with respect to the first body. A seal is provided between the first and second bodies at a position proximate the distal end of the reel.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
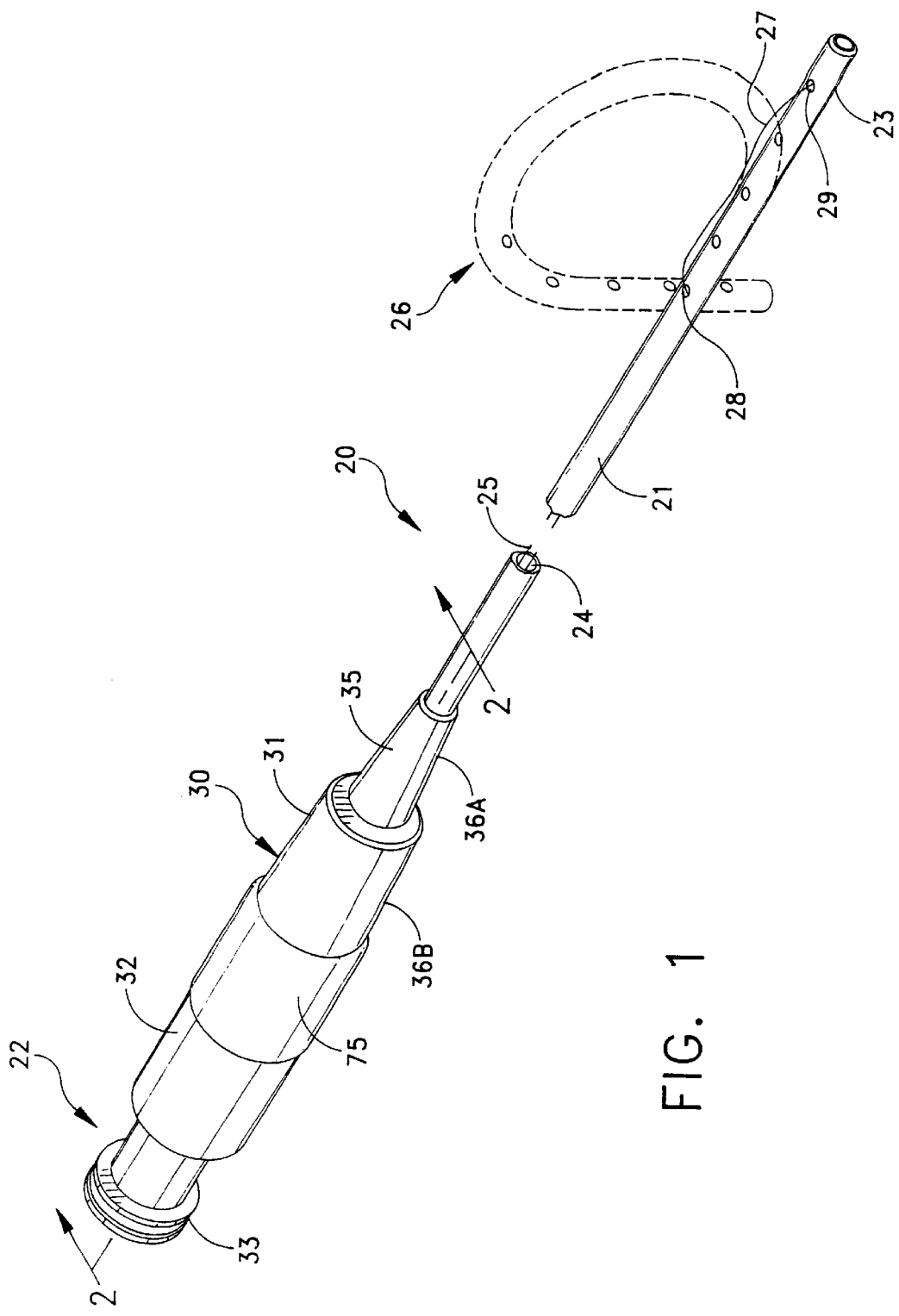
FIG. 1 is a perspective view of a catheter assembly constructed in accordance with this invention.

FIG. 1 depicts a catheter 20 with a radially flexible tube 21 that extends between a proximal end 22 and a distal end 23. A lumen 24 extends through the tube 21 and carries a flexible link 25 in the form of one or more suture threads. A two-part suture thread 25 is shown in FIG. 1. As shown by the solid lines in FIG. 1, the tube 21 extends along an axis when it is inserted and deflects into a pigtail loop 26 as shown by the dashed lines in FIG. 1 when a cannula or other straightening implement is removed from the lumen 24. As known, the pigtail loop 26 constitutes one form of an anchor.

A distal end portion 27 of the suture thread 25 extends through a draw port or aperture 28 displaced from the distal end 23 and a draw port 29 or other connection at the distal end 23. Typically a single suture thread has its mid point located at the distal draw port 29 with the resulting two strands or ports being led proximally through the lumen 24. A locking mechanism 30 constructed in accordance with this invention and located at the proximal end 22 attaches to the ends of the suture strands and includes a first body 31 attached to the flexible tube 21 and a rotatable second body 32 that includes an integral leur connection 33.

When the pigtail loop 26 is straightened for insertion, the suture thread 25 pays out. If the cannula is withdrawn from the lumen 24 through the proximal end 22, the pigtail loop 26 forms such that the draw points 28 and 29 are proximate each other leaving a portion of the suture, i.e., the portion 27, in a loose or slack form. Rotating the second body 32 then draws the strands of the suture thread 25 proximally until the slack introduced by the portion 27 between the draw ports 28 and 29 is eliminated. When the suture thread 25 is taut, it resists any forces that might otherwise tend to straighten the pigtail loop 26 because it locks the distal end 23, particularly the port 29, adjacent the port 28. To remove the catheter 20 in FIG. 1 a surgeon rotates the second body 32 in an opposite direction thereby to loosen the suture thread 25. Thereafter inserting the cannula through the lumen 24 from the proximal end 22 straightens the pigtail loop 26.

Figures 2, 3:
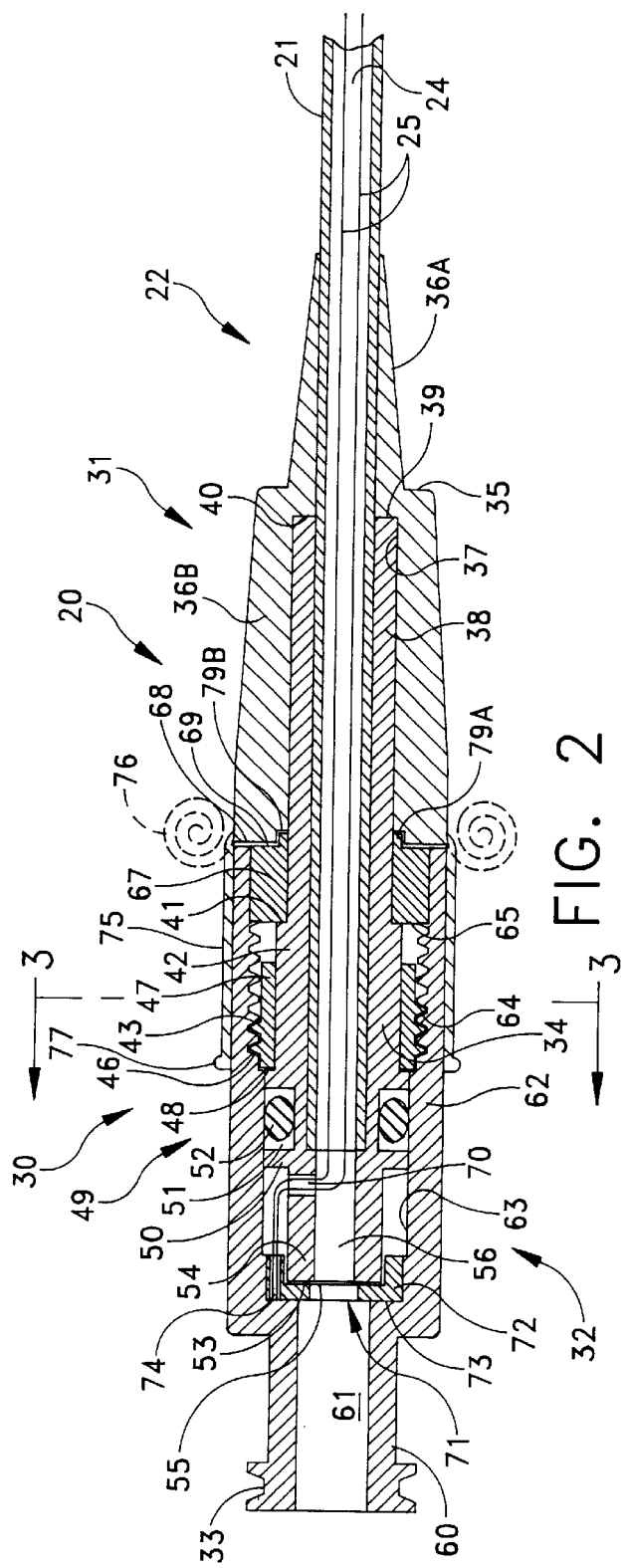
FIG. 2 is a cross section along lines 2—2 in FIG. 1.
FIG. 3 is a cross section along lines 3—3 in FIG. 2.

FIG. 2 is a cross section of one embodiment of a structure that can comprise the control mechanism 30. The first body 31 includes a spindle 34 and a strain relief 35 that includes a proximal tapered end 36A and a body portion 36B that form an axially extending chamber for receiving the flexible tube 21 to a chamber 37 within the spindle 34. The spindle 34 is formed of a molded plastic; the strain relief 35, a somewhat elastic material. The chamber 37 in the strain relief 35 receives the spindle 34, more specifically a tubular extension 38 that is partially coextensive with the chamber 37 and constitutes a first shank. A distal end 39 of the tubular extension 38 abuts a shoulder 40 at the end of the chamber 37.

At the proximal end, the tubular extension 38 terminates in a radial shoulder 41. A portion 42 of the spindle 34 extends proximally from the shoulder 41 and constitutes a second shank that carries a translational nut 43.

As shown in the cross sectional view of FIG. 3, the second shank 42 and translational nut 43 include flats 44 and 45. The flats 44 and 45 limit the translational nut 43 to axial motion without rotation. As shown in FIG. 2, an external surface of the translational nut 43 includes a proximal external thread 46 and a distal annular extension 47.

Still referring to FIG. 2, a radial shoulder 48 defines a proximal stop for the translational nut 43, and it also defines one side of a sealing structure 49 that includes a proximally spaced radial shoulder 50. The shoulders 48 and 50 define an O-ring channel 51 for an O-ring 52. The O-ring 52 effectively seals the area proximally thereof from the area distally thereof. The shoulder 50 also forms the distal end of a spool or reel 53 with a cylindrical central barrel 54 that terminates at a proximal radial end portion 55.

A lumen 56 extends through the spindle 34. The lumen 56 receives the flexible tube 21 and extends the drainage path from the proximal end of the flexible tube 21 to the proximal end of the spindle 34.

The second body 32 has a proximal portion 60 with the leur connection 33 that provides an additional lumen extension 61 of the lumens 24 and 56. As will be apparent from FIG. 2 neither the lumen 56 nor the lumen 61 has a smaller diameter than the lumen 24. Consequently the control mechanism 30 does not impede drainage. The second body also includes a cylindrical cover 62 with a proximal smooth chamber 63 coextensive with the reel 53, an internal intermediate threaded portion 64 for engaging the external threads 46 on the translational nut 43 and a distal end section 65 beyond the threaded portion 64 that is axially coextensive with a portion of the first shank or tubular extension 38. The sealing structure 49 comprising the O-ring channel 51, O-ring 52 and radially adjacent internal surfaces of the first body 31, as previously indicated, prevents drainage material from escaping from the lumen 61 through the interfacing surfaces of the first and second bodies 31 and 32 to the exterior. Tolerances would be selected by known procedures such that sealing would occur while still allowing rotation of the second body 32 relative to the first body 31.

An annular end cap 67 enables the second body 32 to rotate without axial displacement relative to the first body 31. The end cap 67 is affixed to the cover 62 and rotates about the spindle 34. Relative distal axial motion is prevented by interference between a strain relief shoulder 68 and a distal end 69 of the end cap 67; proximal axial motion of the second body 32 is prevented by the interference between the proximal end of the end cap 67 and the radial shoulder 41.

The reel 53 includes a radial port 70 through the barrel 54. The radial port 70 provides a path for the two-parts of the suture thread 25 to pass from the lumens 24 and 55 to be captured in a termination structure 71. The termination structure 71 essentially comprises a cup washer 72 facing distally to be an interface between the proximal end portion 55 of the reel 53 and a radial shoulder 73 formed in the second body proximally of the reel 53.

Axially extending passages 74 through the cup washer 72 at the outer edge thereof serve as structure for affixing the ends of the suture thread 25 by knotting or by adhesive or other means.

Referring now to FIGS. 1 through 3, in use a surgeon typically inserts a stiff cannula through the lumen 61, lumen 56 and lumen 24 until reaching the preformed pigtail 26. The physician then rotates the second body 32 counterclockwise to remove any suture thread from the reel 53. Counterclockwise rotation stops when the translational nut 43 abuts the radial shoulder 48. Thereafter the physician advances the cannula to straighten the pigtail loop 26 and inserts the catheter in a patient. When properly located the physician removes the cannula allowing the pigtail to form in the patient. Then the physician rotates the second body 32 clockwise to take up the slack in the suture thread 25 on the reel 53. While this occurs the translational nut 43 advances distally and provides a positive stop for further rotation when the distal extension 47 of the translational nut 43 engages the end cap 67. As will be apparent the thread pitch will be selected such that an appropriate amount of slack in the suture thread 25 is taken up within the rotation allowed by the two limits imposed on the travel of the translational nut 43.

As will now be described, the manufacture of this catheter assembly avoids complicated processing steps. The first step is forming the spindle 34 on the proximal end of the flexible tube 21. The O-ring 51 can be applied and the suture thread 25 positioned through the draw ports 28 and 29 in FIG. 1 and through the radial port 70. Next the two ends of the suture thread 25 are fed through the axial passages 74 out to an approximate length, knotted proximally of the cup washer 72 and trimmed. At this point the cup washer 72 can be positioned on the proximal end of the reel 53. The translational nut 43 is slid over the flexible tube 21 onto the second shank 42 to the shoulder 46. Now the mandrel is displaced proximally so the pigtail loop 26 forms. Then the second body 32 is slid distally until the threads 46 and 64 on the translational nut 43 and the second body 32, respectively, engage.

For at least the following steps, the unit is mounted on a mandrel so the pigtail loop 26 is straightened. In this particular embodiment, the threads 46 and 64 are left-handed so that clockwise rotation of the second body 32 takes up slack. Consequently, during manufacture the second body 32 is turned counterclockwise to advance the translational nut 43 into the second body 32. Next the second body 32 is advanced distally until the cup washer 72 is captured between the second body 32 and the end portion 55. This produces a positive connection between the second body 32 and the cup washer 72, especially if the mating circumferential surfaces are splined. Consequently, the cup washer 72 is a fixed integral component with the second body 32.

Now the end cap 67 and strain relief 35 are located near the control mechanism 30 and the mandrel is removed again. The pigtail loop 26 reforms introducing slack into the suture thread 25. The second body 32 is rotated clockwise to take up the slack on the reel 53 under visual observation. During this rotation the translational nut 43 advances distally to a final position defined by the position at which the slack is taken up. The distal extension 47 on the translational nut 43 thereupon defines a stop plane. Now the end cap 67 is displaced proximally along the tubular extension 38 until it contacts the extension 47. Then the end cap 67 is affixed, by bonding or otherwise, to the outer shell 62, so the end cap 67 becomes an integral component that rotates with the second body 32 and prevents its axial displacement relative to the first body 31.

Assembly is completed by advancing the strain relief 35 onto the tubular extension until a strain relief shoulder 43 at the proximal end of the strain relief 35 contacts the end cap 67.

As shown in FIGS. 1 and 2, the proximal tapered portion 36A and the distal body portion 36B of the strain relief 35 extend over the flexible tube 21 and the end of the spindle tubular extension 38 distally of the end cap 67. In this specific embodiment, the strain relief 35 also includes a thin, proximally extending, flexible tubular section 75. In FIG. 1 the section 75 is extended and overlies a distal portion of the outer shell 62. In this configuration the section 75 prevents rotation of the second body 32 relative to the first body 31. When such rotation is appropriate, the extension 75 can be rolled distally to form a wrapped cylinder as shown by the dashed wrapped cylinder 76 in FIG. 2. In this configuration the second body 32 can rotate relative to the first body 31. Thus, when extended, the section 78 effectively locks the second body 32. The flexible tubular extension 75 can also terminate with an integrally molded, proximal bead 77 that facilitates the rolling of the section 75.

FIG. 2 also discloses a variation of the end cap 67 in which a proximally extending rib or shoulder 79A lies in a proximally facing channel 79B formed in the strain relief 35. This structure serves as a barrier to prevent adhesive, when used, from reaching the spindle bearing surfaces that are coextensive with the translational nut 43 and end cap 67.

Figure 4:
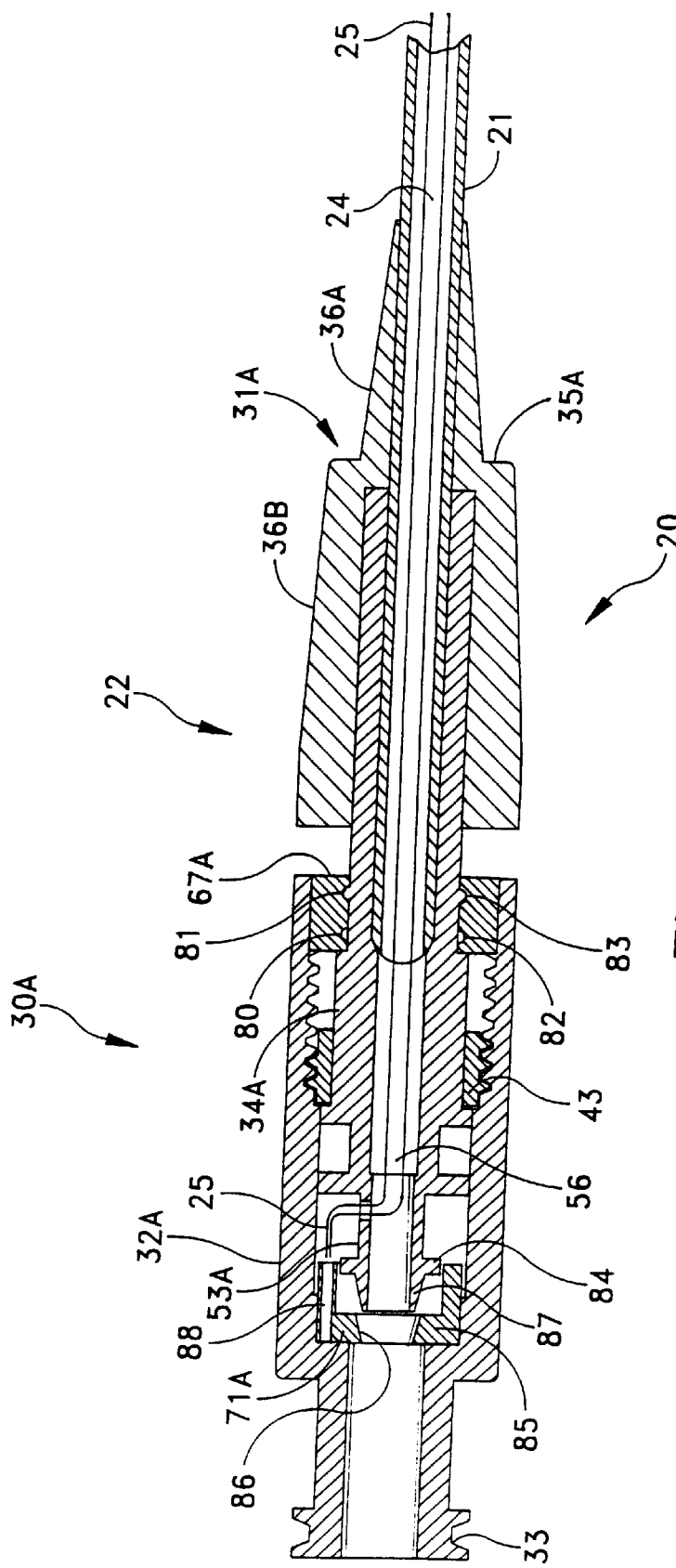
FIG. 4 is a cross section of an alternate embodiment of this invention.
Figure 5:
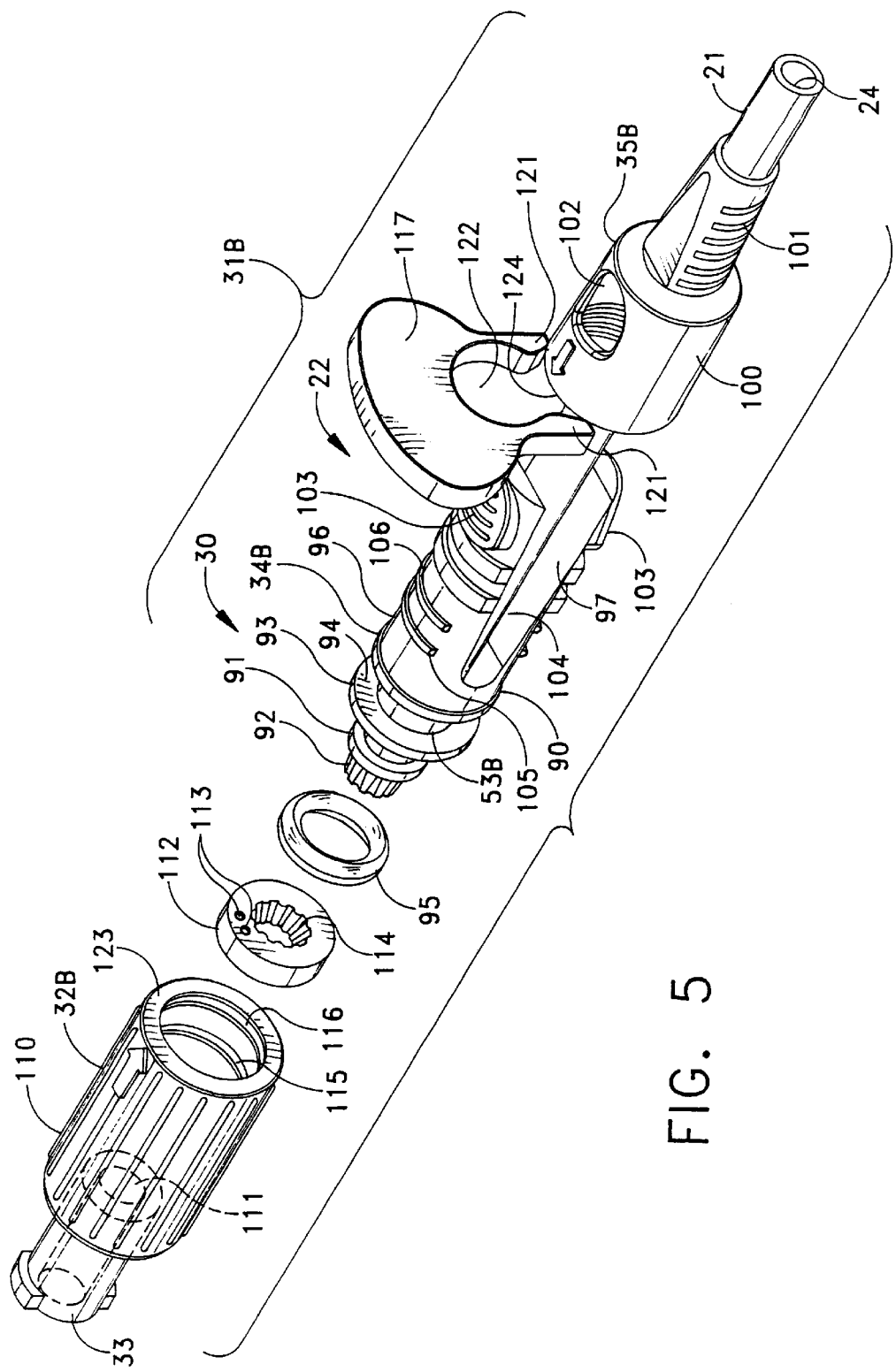
FIG. 5 is an exploded perspective view of another embodiment of this invention.
Figure 6:
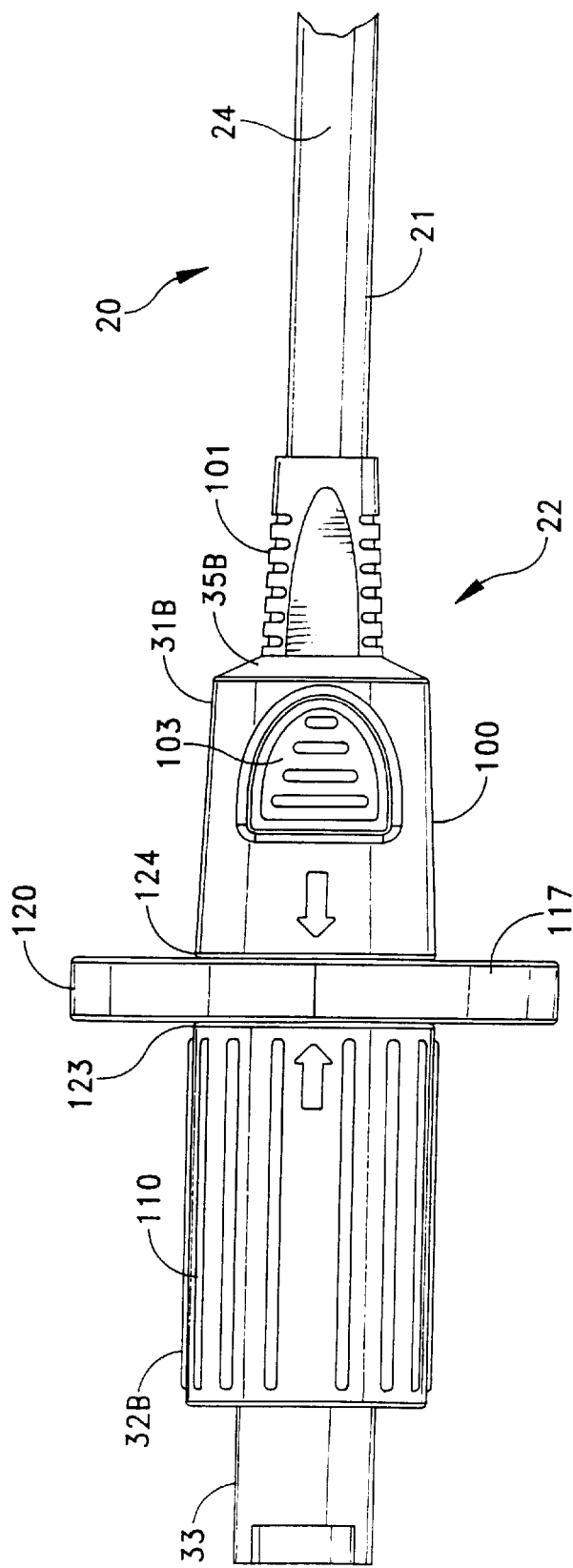
FIG. 6 is a plan view of the embodiment of FIG. 5.
Figure 7:
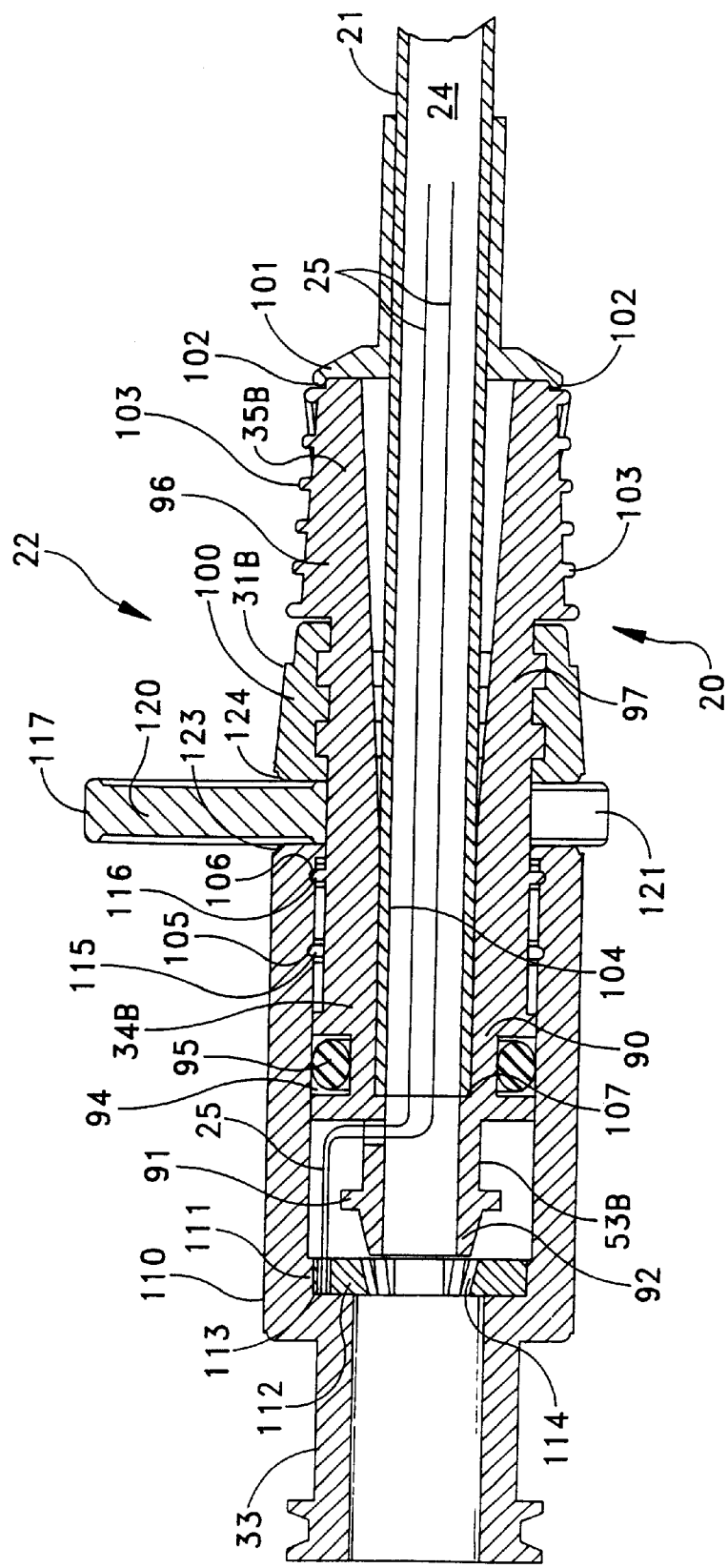
FIG. 7 is a cross section of a portion of the catheter assembly of FIG. 5 in one state.
Figure 8:
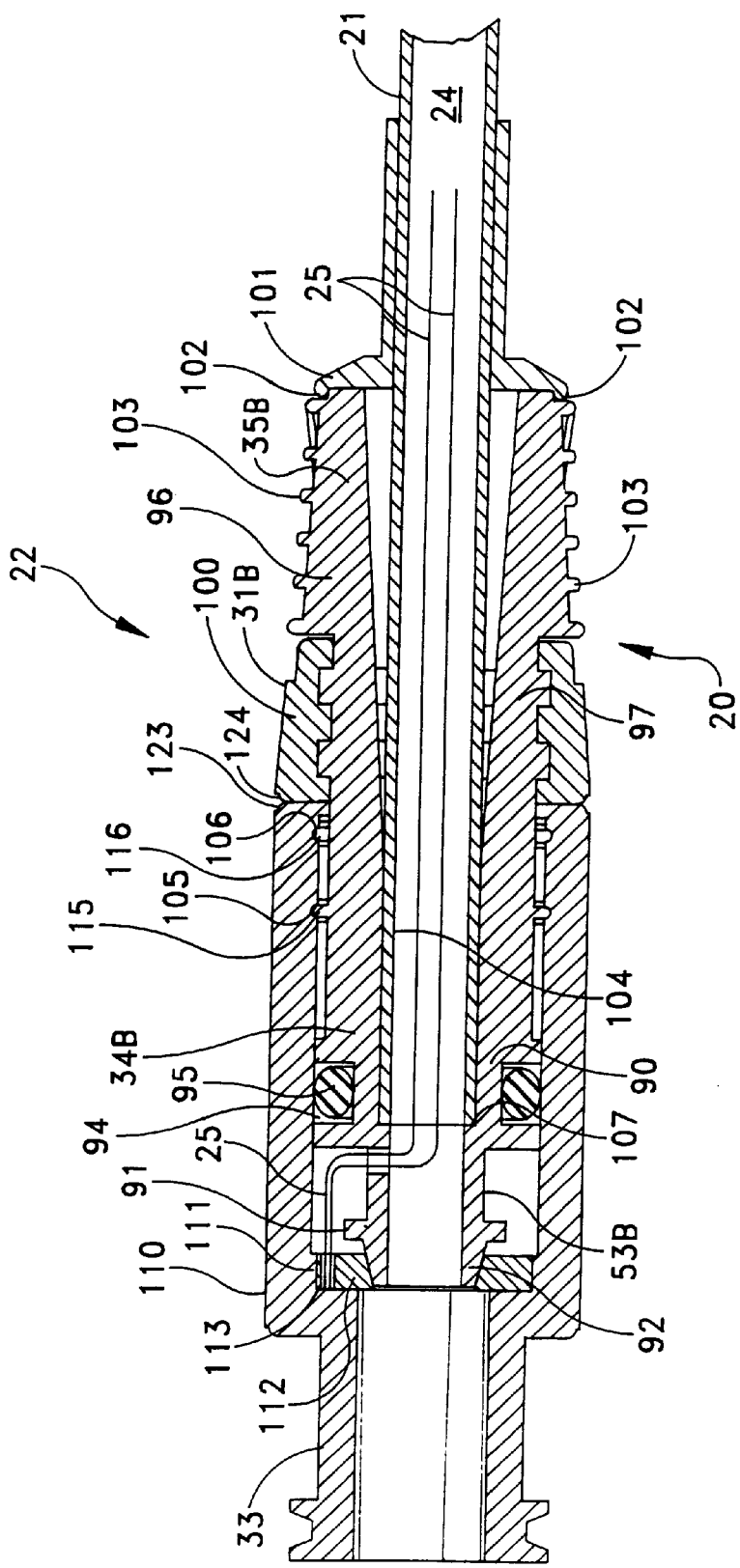
FIG. 8 is a cross section of a portion of the catheter assembly of FIG. 5 in another state.

The specific embodiment shown in FIG. 4 discloses a control mechanism 30A with an alternative locking structure. In this embodiment, only the proximal end 22 of the catheter assembly 20 and a portion of the flexible tube 21 are shown. The specific embodiment is similar in construction to that of the embodiment shown in FIGS. 2 and 3 and like numerals refer to like elements throughout. More specifically, in the embodiment shown in FIG. 4, a strain relief 35A, without the tubular section shown in FIGS. 1 and 2, attaches over a spindle 34A to define a lumen 56 that receives the two-part suture 25. The spindle 34A is like the spindle 34 in FIGS. 2 and 3, but with two modifications. First, an end cap 67A has first and second circumferential grooves 80 and 81 that align, in the position shown in FIG. 4, with detent circumferential beads 82 and 83 formed on the spindle 34A. The resulting detent structure defines a proximal axial position as shown in FIG. 4 wherein the end cap 67A is spaced from the proximal end of the strain relief 35A. There is also a distal axial position that is achieved when the second body 32 is forced distally by a physician to overcome the detent force allowing the second body 32A to advance over the spindle 34A until the end cap 67A abuts the proximal end of the strain relief 35A. This position is also defined as the point at which the proximal detent bead 81 engages the distal detent groove 80.

Still referring to FIG. 4, the reel 53A includes a proximal end flange 84 that is spaced from a termination structure 71A including a cup washer 85 that is formed with a conical, splined surface 86 that corresponds in shape with a splined conical surface 87 extending proximally from the flange 84. In this case the termination structure 71A includes a receptacle or passage 88 that extends axially through the cup washer 85, and the cup washer 85 is coextensive with the spindle 34A including the flange 84 in this retracted position of the second body 32.

In the position shown in FIG. 4, a physician can rotate the second body 32A with respect to the first body 31A and the detent formed by the grooves 80 and 81 and beads 82 and 83 act to prevent inadvertent axial motion of the second body 32A. When the translational nut 43 engages the stop indicating the appropriate amount of slack has been removed from the suture 25, the physician can then apply an axial force to the second body 32A to displace it relative to release the detent and displace it to the position where the end cap 67A abuts the strain relief 35A. This causes the conical surfaces 86 and 87 to engage and produce a positive rotational lock between the spindle 34A and the second body 32A. Thus, in this position it is no longer possible to rotate the second body 32A relative to the first body 31A. To remove the catheter assembly from a patient, the physician would, as previously indicated, insert a stiff cannula to the pig tail loop and then retract the second body 32A to the position shown in FIG. 4. The physician then rotates the second body 32A in an opposite direction to slacken the suture 25 and allow the stiff cannula to be advanced distally and straighten the pig tail loop in the catheter.

It is possible in some applications that the forces applied to the mechanism 30 shown in FIG. 1 and the mechanism 30A shown in FIG. 4 can be sufficient to overcome the detent forces and lock the mechanism inadvertently. The embodiment of FIGS. 5 through 8 provides a structure that minimizes this possibility while retaining other advantages of the prior embodiments. In this particular embodiment a first body 31B includes a spindle 34B and a strain relief 35B attached to the flexible tube 21 while a second body 32B is adapted to rotate relative to the first body 31B. The spindle 34B includes a central spindle body 90 with a reel 53B that is analogous to the reel 53 in FIG. 2 and reel 53A in FIG. 4. A proximal flange 91 defines the proximal end of the reel 53B and supports a proximally extending conical spline member 92. Another radial flange 93 defines an O-ring channel 94 that receives an O-ring 95 so that like the other embodiments the O-ring 95 seals just distally of the reel 53B. A pair of circumferentially-spaced axially extending fingers 96 and 97 extend from the body portion 90 of the spindle 34B and are radially deflectable from a normally expanded position.

A strain relief 35B includes a strain relief body 100 with a proximal tapered extension 101. Diametrically opposed passages 102 are conformed to detent pads 103 at the distal ends of each of the fingers 96 and 97. During manufacture the proximal end of the flexible tube 21 will be inserted into the cavity 104. Then the strain relief 35B is slid over the flexible tube from the distal end thereof. When the strain relief 35B is proximate the detent pads 103, the fingers 96 and 97 can be deflected radially together. The strain relief 35B can pass proximally over the detent pads 103 and advance until the fingers 96 and 97 deflect outward and the detent pads 103 enter the radial openings 102 thereby locking the spindle 34B and the strain relief 35B together.

The second body 32B includes a cylindrical body portion that supports the leur connection 33 from its proximal end and has a seat 111 at the proximal end of the body portion 110 for receiving a termination structure 112 that is in the form of a radial washer 112 with axially extending passages 113 for receiving the ends of the suture 25 and a splined conical receiving section 114.

At the distal end of the cylindrical body 111 there are formed two circumferential detent grooves shown as a proximal detent groove 115 and a distal detent groove 116. In the position shown in FIG. 7, the detent grooves 115 and 116 engage the circumferential detents 105 and 106, respectively, thereby to space the second body 32B from the strain relief 35B.

While the detents can provide some protection against accidental axially displacement of the second body 32B, this embodiment also includes a generally unshaped insert 117 with a radially extending planar body portion 120 from which a pair of legs 121 extend to define a central opening 122. As the insert 117 is displaced in a radial plane toward the spindle 34B, the legs 121 will expand slightly to allow the central portion 122 to wrap about the structure of the fingers 96 and 97 thereby produce a snap action to lock the insert 111 in place. The insert body portion 120 facilitates the insertion of the catheter by providing a surface that the physician can use when the catheter is being inserted or removed from a patient.

The operation of this control mechanism 30B is similar to the embodiments of FIGS. 2 and 4. A physician initially straightens the flexible tube 21 by inserting a stiff cannula. In the embodiment of FIGS. 5 through 8 this occurs with the insert 117 in place. When the distal end of the catheter is properly placed, the cannula can be removed so the pig tail forms. Then the second body 32B can be rotated without axial displacement to take up any slack in the suture 25. Rotation continues for either a predetermined number of turns or until the physician's tactile senses indicate that the suture 25 is taut. The insert 117 is removed and the physician applies an axial force in a distal direction to the second body 32B to overcome the retaining force of the detents. The second body 32B thereupon advances until the detent groove 115 engages the detent bead 106. At this point the distal end surface of the second body 32B engages a proximal end surface of the first body 31B. At the same time the splined conical surface 92 engages the splined surface 114. Consequently no further rotation of the second body 32B can be achieved.

On removal, the physician retracts the second body 32B to release the locking function of the conical splined surfaced 92 and 114. A stiff cannula can be inserted until it engages the pig tail. At that point the physician can unwrap the sutures from the reel 53B by rotating the second body 32B. Then the physician advances the cannula to straighten the pig tail and withdraw the catheter assembly from the patient with or without the insert 117 in place.

This invention has been disclosed in terms of three different embodiments. Each has particular advantages particularly adapted for different modalities and preferences for individual physicians. In each, however, slack in a suture thread produced when an anchor structure forms is taken up by wrapping the suture thread on a reel. In each a sealing structure is formed proximate to and distally of the reel thereby to prevent any drainage material from leaking from the structure. Each of these systems is readily and easily manufactured at acceptable cost. Moreover, each of the systems is reliable and easy to use, particularly as the rotation occurs independently of any axial movement in any of the embodiments with the embodiment of FIG. 2 having no method of producing any axial motion. Each also can include a positive locking mechanism to prevent inadvertent rotation.

This invention has been disclosed in terms of certain embodiments. It will be apparent that many modifications can be made to the disclosed apparatus without departing from the invention. Beyond changes to specific structural features of the various control mechanisms, each control mechanism can be used with the specifically disclosed pigtail loop as an anchor or other type of known anchors, such as tulip, foraminous, Malecot and Amplatz anchors. Therefore, it is the intent of the appended claims to cover all such variations and modifications as come within the true spirit and scope of this invention.

What is claimed as new and desired to be secured by Letters Patent of the United States is:

1. A catheter assembly comprising:
    A) a flexible tube with an anchor at a distal end of said tube,
    B) a first body affixed to a proximal end of said tube with a first passage extending along an axis and being formed as an extension of said tube and with a reel disposed at the proximal end having a radial aperture therethrough,
    C) a suture extending from said anchor through said lumen, said first passage and said radial aperture,
    D) a second body concentric with a portion of said first body, said second body including a second axial passage as an extension of said first axial passage and a termination for receiving the suture extending from said radial aperture, said second body being rotatable about the axis without axial displacement with respect to said first body, and
    E) a seal formed between said first and second bodies at a position proximate to and distally of said reel.

2. A catheter assembly as recited in claim 1 wherein said reel has a distal radial surface, said termination including a portion intermediate said radial reel surface and said second body.

3. A catheter assembly as recited in claim 2 wherein said seal includes an O-ring closely adjacent said reel and said first body has a reduced diameter first shank portion spaced distally of the O-ring and wherein said catheter assembly additionally comprises a retainer intermediate said first shank portion and said second body for preventing proximal motion of the said second body with respect to said first body.

4. A catheter assembly as recited in claim 3 wherein said termination is formed with a distally extending cylindrical portion overlying a portion of the reel adjacent said radial reel surface.

5. A catheter assembly as recited in claim 4 wherein said first body includes a second shank portion intermediate said reel and said first shank portion with a proximal shoulder adjacent said proximal end of said seal and wherein said catheter assembly further includes an axially translatable member on said second shank portion having a plurality of external teeth and said second body having a plurality of internal teeth, rotation of said second body in a first direction causing said suture to wrap on said reel being limited when said translational member reaches said proximal shoulder.

* * * * *